(12) United States Patent
Rubin et al.

(10) Patent No.: US 6,535,835 B1
(45) Date of Patent: Mar. 18, 2003

(54) ANGLE INDEPENDENT ULTRASOUND VOLUME FLOW MEASUREMENT

(75) Inventors: Jonathan M. Rubin, Ann Arbor, MI (US); Jeffrey Brian Fowlkes, Ann Arbor, MI (US); Theresa Ann Tuthill, Ann Arbor, MI (US); Anne Lindsey Hall, New Berlin, WI (US)

(73) Assignees: GE Medical Systems Global Technology Company, LLC, Waukesha, WI (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/495,231

(22) Filed: Jan. 31, 2000

(51) Int. Cl.[7] .................. G01B 11/02; G01B 11/14; G01B 13/02; G01B 21/02; G01B 5/02
(52) U.S. Cl. .............................. 702/159; 702/48
(58) Field of Search .................. 702/159, 48, 49; 600/443, 454; 73/861.25; 128/661.01; 382/128

(56) References Cited

U.S. PATENT DOCUMENTS

| | | | |
|---|---|---|---|
| 4,265,126 A | * 5/1981 | Papadofranakis et al. ............. | 73/861.25 |
| 5,349,524 A | 9/1994 | Daft et al. | |
| 5,398,216 A | 3/1995 | Hall et al. | |
| 5,505,204 A | 4/1996 | Picot et al. | |
| 5,573,001 A | * 11/1996 | Petrofsky et al. ...... | 128/661.01 |
| 5,617,862 A | * 4/1997 | Cole et al. ............ | 128/661.01 |
| 5,676,147 A | * 10/1997 | Petrofsky et al. ...... | 128/661.01 |
| 5,682,896 A | 11/1997 | Scheib et al. | |
| 5,793,883 A | * 8/1998 | Kim et al. ............... | 382/128 |
| 5,934,288 A | 8/1999 | Avila et al. | |
| 5,997,480 A | 12/1999 | Sumanaweera et al. | |
| 6,029,116 A | * 2/2000 | Wright et al. .......... | 702/32 |
| 6,186,949 B1 | * 2/2001 | Hatfield et al. ........ | 600/443 |
| 6,193,659 B1 | * 2/2001 | Ramamurthy et al. ... | 600/443 |
| 6,213,946 B1 | * 4/2001 | Brock-Fisher ......... | 600/443 |
| 6,213,947 B1 | * 4/2001 | Phillips ............... | 600/443 |
| 6,213,950 B1 | * 4/2001 | Cespedes et al. ...... | 600/454 |
| 6,221,018 B1 | * 4/2001 | Ramamurthy et al. ... | 600/443 |
| 6,245,016 B1 | * 6/2001 | Daft et al. ............ | 600/443 |

FOREIGN PATENT DOCUMENTS

| | | |
|---|---|---|
| EP | 0 541 342 A1 | 5/1993 |
| EP | 0 839 497 A1 | 5/1998 |

OTHER PUBLICATIONS

Van Der Steen, et al., "In Vivo Validation of Blood Flow Estimation Using the Decorrelation of Radiofrequency Intravascular Echo Signals," 1997 IEEE Ultrasonics Symposium, pp. 1247–1250, (1997).

Li, et al., "Quantification of Blood Volume Flow by Decorrelation Analysis of Radio–Frequency Intravascular Echo Signals," IEEE Computers in Cardiology 1997, 24:1–4, (1997).

Speckle Decorrelation Flow Measurement with B–Mode US of Contrast Agent Flow in a Phantom and in Rabbit Kidney, Rubin et al., Radiology, vol. 213, No. 2., pp. 429–437, (1999).

(List continued on next page.)

*Primary Examiner*—John Barlow
*Assistant Examiner*—Aditya S Bhat
(74) *Attorney, Agent, or Firm*—McAndrews, Held & Malloy, Ltd.; Peter J. Vogel; Michael A. Dellapenna (57) ABSTRACT

The volume of fluid flow within a vessel (VE) is measured by an ultrasound system. Ultrasound waves backscattered from the fluid within the vessel generate data from which velocity values representing components of velocity ($V_x$ and $V_y$) of the fluid flow in the scan plane (IP) are calculated. Grayscale data is correlated and the rate of decorrelation (D) of the data is calculated. The volume flow of the fluid (F) is estimated in response to the velocity signals and the rate of decorrelation (D).

34 Claims, 4 Drawing Sheets

OTHER PUBLICATIONS

Multi–Dimensional Velocity Estimation with Ultrasound Using Spatial Quadrature, Anderson, Martin E., IEEE Transactions on Ultrasonics, Ferroelectrics and Frequency Control, vol. 45, No. 3, pp. 852–861, (1998).

Ultrasound Doppler Probing of Flows Transverse with Respect to Beam Axis, Newhouse, et al., IEE Transactions on Biomedical Engineering, vol. BME–34, No. 10, pp. 779–789, (1987).

Ultrasonic Estimation of Tissue Perfusion: A Stochastic Approach, Adler, et al., Ultrasound in Med. & Biol., vol. 21, No. 4, pp. 493–500, (1995).

Methods for Estimation of Statistical Properties of Envelopes of Ultrasonic Echoes from Myocardium, Wear, Keith A., IBEE Transactions on Medical Imaging, vol. MI–6, No. 4, pp. 281–291, (1987).

A Double Beam Doppler Ultrasound Method for quantitative Blood Flow Velocity Measurement, Ultrasound in Med. & Bio., vol. 8, No. 4, pp. 421–425, (1982).

Time Domain Formulation of Pulse–Doppler Ultrasound and Blood Velocity Estimation by Cross Correlation, Bonnefous et al., Ultrasonic Imaging, vol. 8, pp. 73–85 (1986).

American Institute of Ultrasound in Medicine Proceedings, J. Ultrasound Med. 7:S39–S283, 1988.

Decorrelation of Intravascular Echo Signals: Potentials for Blood Velocity Estimation, Wenguang, et al., J. Accoust. Soc. Am 102, 3785–3794; (1997).

Determination of Scan–Plane Motion Using Speckle Decorrelation: Theoretical Considerations and Initial Test, Chen et al., vol. 8, 38–44, (1997).

A New Method for Estimation of Velocity Vectors, Jensen et al., IEEE Transactions on Ultrasonics, Ferroelectrics and Frequency Control., vol. 45, No. 3, 837–851 (1998).

FLASH Correlation: A New Method for 3–D Ultrasound Tissue Motion Tracking and Blood Velocity Estimation, Morsy et al., IEEE Transactions on Ultrasonics, Ferroelectrics, and Frequency Control, vol. 46, No. 3, (1999).

Angle Independent Ultrasonic Detection of Blood Flow, Trahey, et al., IEEE Transactions on Biomedical Engineering, vol., BME–34 No. 12, (1987).

Automated Three–dimensional US Frame Positioning Computed from Elevational Speckle Decorrelation, Tuthill, et al., Radiology; 209: pp. 575–582 (1998).

Autocorrelation of Integrated Power Doppler Signals and its Application, Chen et al., Ultrasound in Med. & Biol., vol. 22 No. 8 pp. 1053–1057, 1996.

* cited by examiner

ANGLE INDEPENDENT ULTRASOUND VOLUME FLOW MEASUREMENT

BACKGROUND OF THE INVENTION

The Background of the Invention will be explained with the aid of the numbered references which appear at the end of this section of the specification. The quantification of volumetric fluid (e.g., blood) flow would be beneficial for a number of applications, including clinical applications, such as diagnosis of heart disease, cartoid stenosis, coronary arteriosclerosis, and renal failure. Doppler is the current clinical standard for measuring blood flow with ultrasound. Fluid motion towards or away from an ultrasound beam pulse modifies the wavelength of the insonifying pulse. Assuming the angle between the beam and the orientation of a fluid-carrying vessel (e.g., blood vessel) are known, the velocity of fluid flow in the vessel then is computed from the resulting Doppler frequency shift. Current techniques for volume flow measurement require a sonographer to orient the center axis of the vessel in the scan plane of the ultrasound beam, and then to calculate the total flow volume assuming a circularly symmetrical lumen. These assumptions, which are often not true, lead to large errors, making the method very difficult to apply.

The use of multiple Doppler beams to determine in-plane flow velocities (i.e., velocities in the ultrasound beam scan plane) have been known for many decades (Wang, 1982) [1]. Using two co-planar beams and trigonometric relations, the derived measured velocity is angle independent.

The cross-correlation of consecutive ultrasound A-lines eliminates the aliasing ambiguity of Doppler (Bonnefous 1986) [13].

Speckle tracking, the correlation of patterns between sequential frames, has been used to determine 1-D and 2-D flow vectors (Trahey 1987) [2]. With the development of volumetric ultrasound scans, the correlation search algorithm has been applied in 3-D with some success (Morsy 1999) [3].

One of the first techniques to quantify the magnitude of the non-axial flow components was developed by Newhouse (1987) [4] and is based on spectral broadening of the ultrasound RF signal.

More recently, Anderson (1998) [5] used a spatial weighting of the point spread function to quantify the lateral motion. In a similar study, Jensen (1998) [6] applied a transverse spatial modulation generated by apodization of the transducer elements to quantify flow in one or two directions transverse to the axial flow. Both of these techniques only determine 2-D flow.

The estimation of blood velocity using the decorrelation of echo signals has also been fairly well documented. Using the time rate-of-change of A-lines, Bamber (1988) [7] demonstrated that decorrelation could be used to image tissue motion and blood flow. More quantitatively, Li et al (1997) [8] showed that the decorrelation of RF signals was linearly related to the lateral displacement. The detection of variations in contrast-enhanced blood flow using grayscale decorrelation has also been previously shown in animal studies (Rubin, 1999) [9].

References

[1] Wang W, Yao L. A double beam Doppler ultrasound method for quantitative blood flow velocity measurement. Ultrasound Med Biol 1982;8:421–425.

[2] Trahey G E, Allison J W, von Ramm O T, Angle independent ultrasonic detection of blood flow. IEEE Trans Biomed Eng 1987;34:965–967.

[3] Morsy A A, von Ramm O T. FLASH correlation: A new method for 3-D ultrasound tissue motion tracking and blood velocity estimation. IEEE Trans Ultra Ferro Freq Con 1999;46:728–736.

[4] Newhouse V L, Censor D, Vontz T, Cisneros J A, Goldberg B B. Ultrasound Doppler probing of flows transverse with respect to beam axis. IEEE Trans Biomed Eng 1987;34:779–789.

[5] Anderson M E. Multi-dimensional velocity estimation with ultrasound using spatial quadrature. IEEE Trans Ultra Ferro Freq Con 1998;45:852–861.

[6] Jensen J A, Munk P. A new method for estimation of velocity vectors. IEEE Trans Ultra Ferro Freq Con 1998;45:837–851.

[7] Bamber J, Hasan P, Cook-Martin G, Bush N. Parametric imaging of tissue shear and flow using B-scan decorrelation rate (abstr). J Ultrasound Med 1988;7:S135.

[8] Li W G, Lancee C T, Cespedes E I, vanderSteen A F, Bom N. Decorrelation of intravascular echo signals: Potentials for blood velocity estimation. J Acoust Soc Am 1997;102:3785–3794.

[9] Rubin J M, Fowlkes J B, Tuthill T A, Moskalik A P, Rhee R T, Adler R S, Kazanjian S, Carson P L, Speckle decorrelation flow measurement with B-mode US of contrast agent flow in a phantom and in rabbit kidney. Radiology 1999;213;429:437.

[10] Tuthill T A, Krücker J F, Fowlkes J B, Carson P L Automated three-dimensional US frame positioning computed from elevational speckle decorrelation. Radiology 1998;209:575–582.

[11] Wear K A, Popp R L. Methods for estimation of statistical properties of envelopes of ultrasonic echoes from myocardium. IEEE Trans Med Imag 1987;6:281–291.

[12] Adler R S, Rubin J M, Fowlkes J B, Carson P L, Pallister J E. Ultrasonic estimation of tissue perfusion: a stochastic approach. Ultrasound Med Biol 1995;21:493–500.

[13] Bonnefous O, Pesque P. Time domain formulation of pulse-Doppler ultrasound and blood velocity estimation by cross correlation. Ultrasonic Imag 1986;8:73–85.

[14] Chen J, Fowlkes J B, Carson P L, Rubin J M. Determination of scan-plane motion using speckle decorrelation: theoretical considerations and initial test. Int J Imaging Syst Technol 1997;8:38–44.

[15] Chen, J R, Fowlkes J B, Carson P L, Rubin J M, Adler R S. Autocorrelation of integrated power Doppler signals and its application. Ultrasound Med. Biol. 1996; 22: 1053–1057.

BRIEF SUMMARY OF THE INVENTION

The preferred embodiment is useful in an ultrasound system for measuring the volume of fluid flow within a region of interest. In such an environment, ultrasound waves are transmitted to the vessel in transmit directions defining a scan plane, preferably by an ultrasound transducer. Data signals are generated in response to ultrasound waves backscattered from the fluid within the vessel. Velocity signals having velocity values representing components of velocity of the fluid flow in the scan plane are generated in response to data generated from the data signals. Portions of the data are correlated, and the rate of decorrelation of the portions is calculated. The volume of flow of the fluid is estimated in response to the velocity signals and the rate of decorrelation.

The techniques preferably are implemented with an ultrasound transducer and a data processor.

By using the foregoing techniques, the volume of fluid flow in a vessel can be determined independent of scan angle and without making any assumptions about vessel shape or flow geometry. For example, the techniques permit true blood volume flow estimates without any of the assumptions typically made with the above-described prior methods. The techniques of the preferred embodiment can be incorporated into most of the standard ultrasound transducer array scanheads now on the market. The techniques are robust and can be implemented in real time.

DETAILED DESCRIPTION OF THE INVENTION

Figure 1:
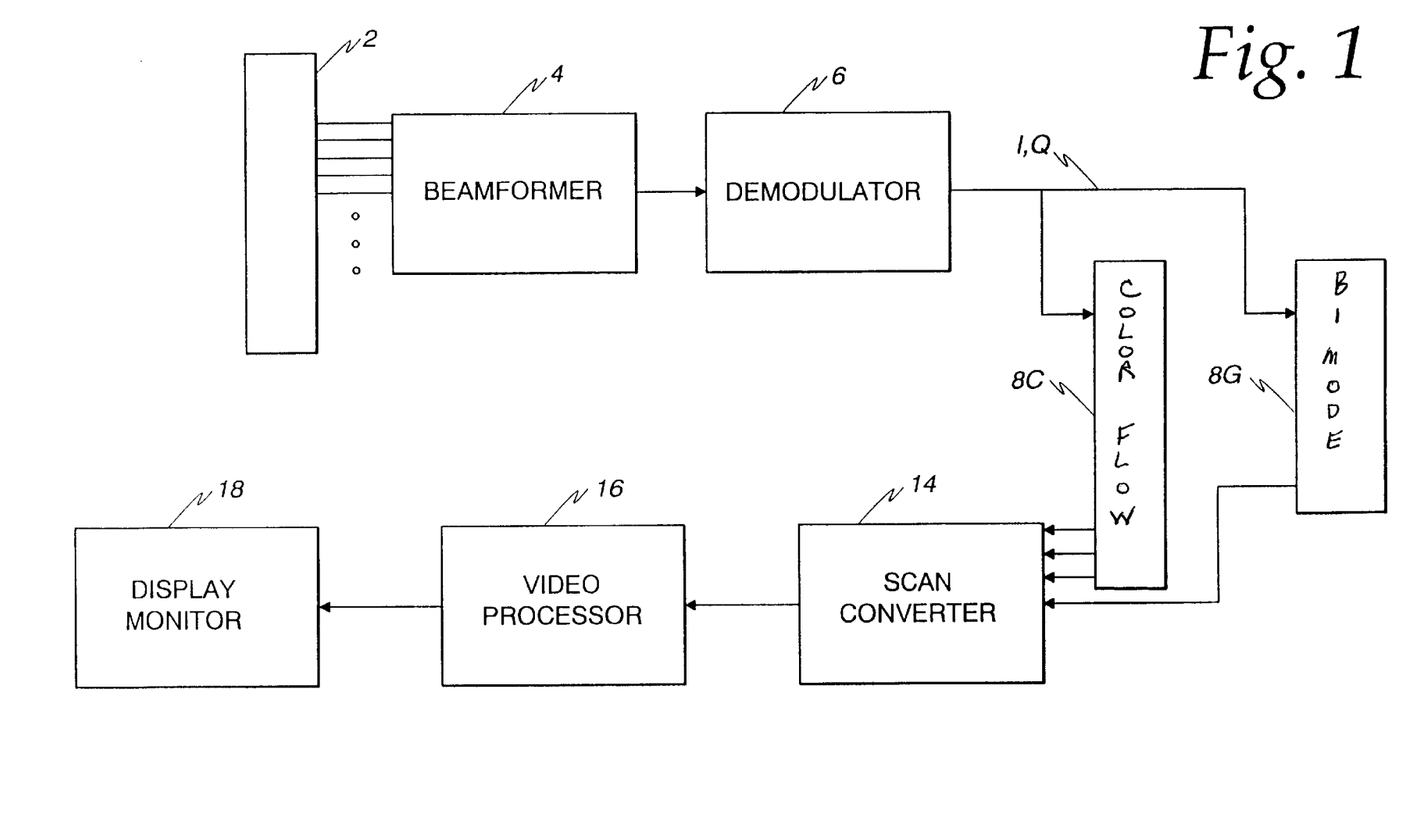
FIG. 1 is a schematic block diagram showing the signal processing chain for a color flow and B-mode ultrasound imaging system suitable for use in connection with the preferred embodiment.

Referring to FIG. 1, the basic signal processing chain for a color flow and gray scale imaging system suitable for an embodiment of invention comprises an ultrasound transducer array 2, which is activated to transmit pulse sequences comprising tone bursts of length P which are fired repeatedly at a pulse repetition frequency (PRF) which typically is in the kilohertz range. The pulse sequences, including burst lengths P, are different for the color flow and B-mode processing. For color flow imaging, P may be 4 to 8 cycles, and the tone bursts are focused at the same transmit focal position with the same transmit characteristics.

A series of color flow transmit firings focused at the same transmit focal position are referred to as a "packet". Each transmit beam propagates through the object being scanned and is reflected by ultrasound scatterers in the object.

The return RF signals are detected by the transducer elements and received by the respective receive channels in the beamformer 4. The beamformer sums the delayed channel data and outputs in a beam summed signal which is demodulated into in-phase and quadrature (I/Q) signal components by a demodulator 6. The B-mode I, Q outputs from demodulator 6 are transmitted to a mid processor 8G for gray scale B-mode processing, and the color flow I, Q outputs from demodulator 6 are transmitted to a midprocessor 8C for color processing.

Figure 2:
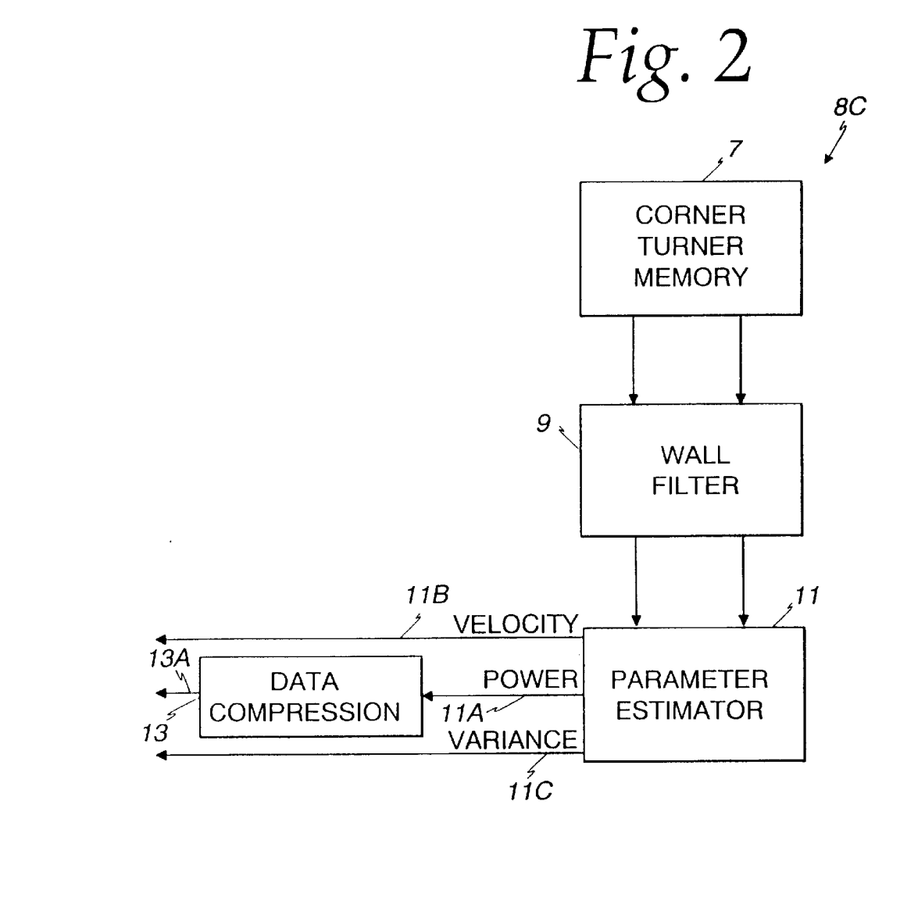
FIG. 2 is a schematic block diagram showing the mid processor color flow apparatus illustrated in FIG. 1.

FIG. 2 illustrates mid-processor 8C. The I/Q signal components from demodulator 6 are stored in a corner turner memory 7, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through a wall filter 9 which rejects any clutter corresponding to stationary or very slow-moving tissue. The filtered outputs are then fed into a parameter estimator 11, which converts the range cell information into the intermediate autocorrelation parameters N, D and R(0). N and D are the numerator and denominator for the autocorrelation equation, as shown below:

$$N = \sum_{i=1}^{M-1} (I_i Q_{i+1} - I_{i+1} Q_i) \quad (A)$$

$$D = \sum_{i=1}^{M-1} (I_i I_{i+1} + Q_i Q_{i+1}) \quad (B)$$

where $I_i$ and $Q_i$ are the demodulated, basebanded input data for firing i, and M is the number of firings in the packet. R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (C)$$

R(0) represents the color flow power of the backscatter from the color flow transmit firings.

A processor converts N and D into a magnitude and phase for each range cell. The equations used are as follows:

$$\phi(T) = \tan^{-1}\left[\frac{N}{D}\right] \quad (E)$$

R(T) and $\phi$(T) are the magnitude and phase, respectively, of the first lag autocorrelation function. The term lag is used to indicate a time interval. For example, a lag may be a frame-to-frame increment or a firing-to-firing increment. As indicated by equations (A)–(C), the exact autocorrelation functions are approximated by finite sums over the known data in the number of firings in a packet.

The parameter estimator processes the magnitude and phase values into signals having values representing estimates of power, velocity and turbulence or variance which are transmitted on conductors 11A, and 11B and 11C, respectively. The phase is used to calculate the mean Doppler frequency, which is proportional to the velocity as shown below; R(0) and |R(T)| (magnitude) are used to estimate the turbulence.

The mean Doppler frequency in hertz is obtained from the phase of N and D and the pulse repetition from T:

$$\bar{f} = \frac{1}{2\pi T} \tan^{-1}\left[\frac{N}{D}\right] = \frac{1}{2\pi T}(\phi(T)) \quad (F)$$

The mean velocity is calculated using the Doppler shift equation below. Since θ, the angle between the flow direction and the sampling direction, is not known, cos θ is assumed to be 1.0.

$$\bar{v} = \frac{\bar{f}}{f_o} \frac{c}{2\cos\theta} \quad (G)$$

Preferably, the parameter estimator does not calculate the mean Doppler frequency as an intermediate output, but calculates v̄ directly from the phase output of the processor using a look-up table. However, any velocity estimator can be used for purposes of the calculations shown in equations (1)–(6) described later. The velocity estimations may include delay cross correlation, autoregression etc.

The turbulence may be calculated in the time domain as a second-order series expansion of the variance of the mean Doppler frequency. The time domain expression for turbulence involves calculating the zero-lag and one-lag autocorrelation functions, R(0) and R(T), respectively.

The time domain expression for turbulence may be expressed as:

$$\sigma^2 = \frac{2}{(2\pi T)^2} \left[1 - \frac{|R(T)|}{R(0)}\right] \quad (H)$$

The mean value signal $\phi(T)$ is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, involving a mixture of many velocities. To indicate the strength of the signal from the flowing reflectors, the signal R(0) indicates the amount of the returned power in the Doppler-shifted flow signal.

The signal power on conductor 11A is passed through a data compression module 13 which compresses the data according to families of data compression curves. A different family of curves can be provided for different scanning applications. For example, one family of curves is provided for renal scanning, while another family of curves is provided for carotid artery scanning. Controller 26 sets the default curve when a user selects the scan application. The dynamic range controls the range of intensities or lumens created on display 18.

Figure 3:
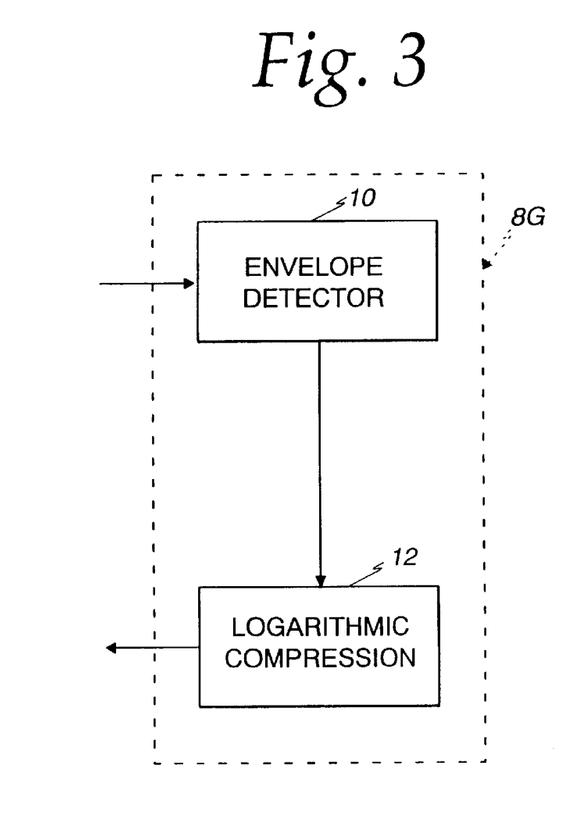
FIG. 3 is a schematic block diagram showing the mid processor B-mode apparatus illustrated in FIG. 1.

Referring to FIG. 3, gray scale B-mode mid-processor 8G includes an envelope detector 10 for forming the envelope of the beamsummed receive signal by computing the quantity $(I^2+Q^2)^{1/2}$. The envelope of the signal undergoes some additional B-mode processing, such as logarithmic compression (block 12 in FIG. 3), to form display data which is output to the scan converter 14 (FIG. 1).

Referring again to FIG. 1, the color flow estimates and gray scale display data are sent to the scan converter 14, which converts the data into X-Y format for video display. The scan-converted frames in X-Y format are passed to a video processor 16, which basically maps the video data to a display color map and gray scale image frames for video display. The image frames are then sent to the video monitor 18 for display. Typically, for color images, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

The images displayed by the video monitor 18 are produced from an image frame of data in which each datum indicates the intensity or brightness of a respective pixel in the display, as well as the flow velocity. An image frame may, e.g., comprise a data array in which each intensity datum is a binary number that indicates pixel color and brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed and a color value which indicates flow mean velocity and/or power.

Figure 4:
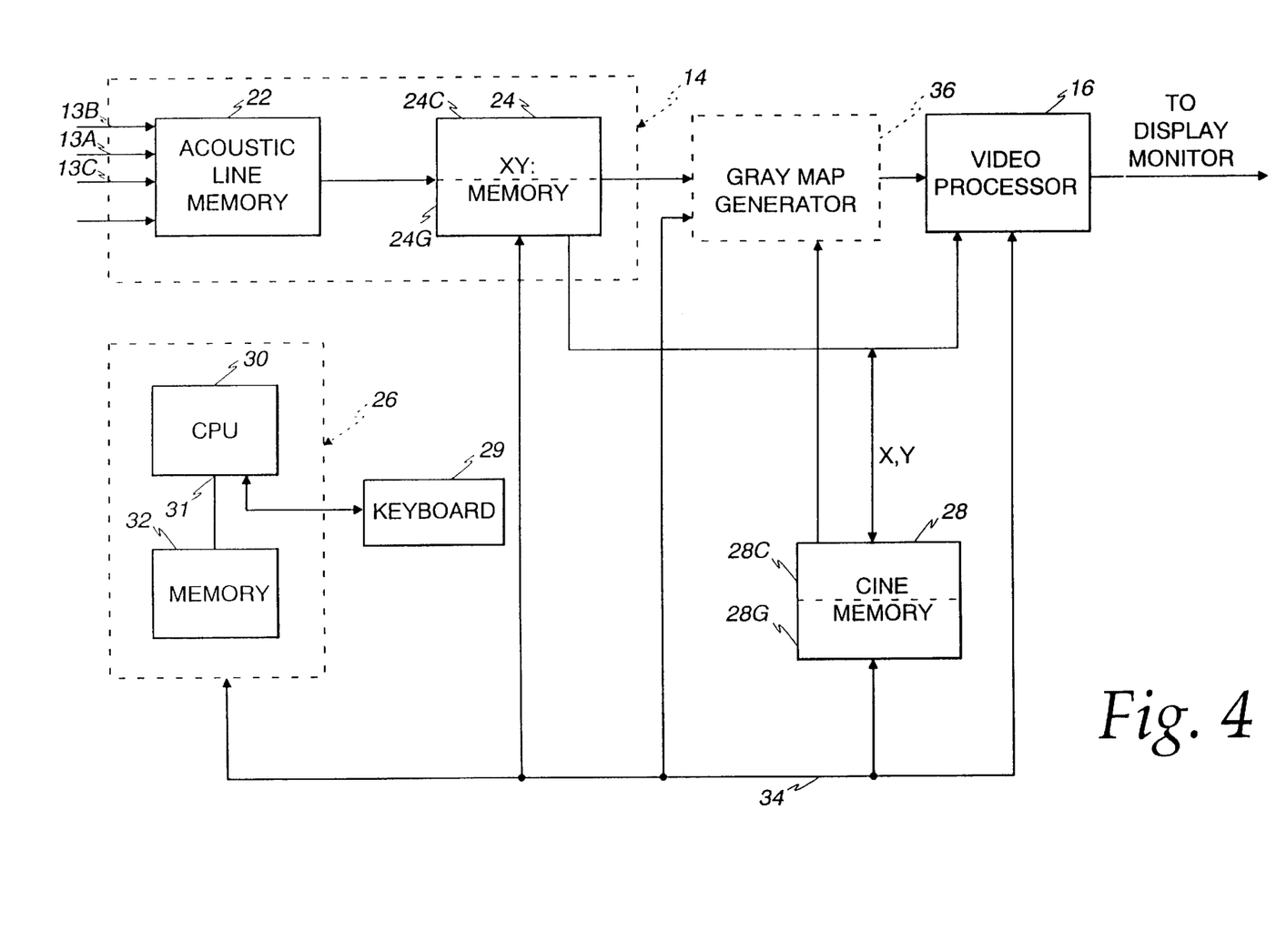
FIG. 4 is a schematic block diagram showing additional details of portions of the system illustrated in FIG. 1.

Referring to FIG. 4, system control is centered in a master controller or host computer 26, which accepts operator inputs through an operator interface (not shown) and in turn controls the various subsystems. The master controller 26 also generates the system timing and control signals. The master controller 26 comprises a central processing unit (CPU) 30 and a random access memory 32. A keyboard 29 is used to enter data into CPU 30. The CPU 30 has read only memory incorporated therein for storing routines used in constructing gray and color maps based on acquired raw data.

The scan converter 14 comprises an acoustic line memory 22 and an X-Y memory 24. The B-mode and color mode intensity data stored in polar coordinate (R-θ) sector format in acoustic line memory 22 is transformed to appropriately scaled Cartesian coordinate pixel display data, which is stored in X-Y memory 24. The color data is stored in memory locations 24C, and the gray scale data is stored in memory locations 24G. The scan-converted frames are passed to video processor 16, which maps the data to a gray map for video display. The gray scale image frames are then sent to the video monitor for display.

Successive frames of acoustic sample data are stored in cine memory 28 on a first-in, first-out basis. Color frames are stored in memory locations 28C, and gray scale frames are stored in memory locations 28G. In the color region of interest, for every word of color data corresponding to a display pixel, there is a corresponding word of B-mode gray scale data corresponding to that pixel. The cine memory is like a circular image buffer that runs in the background, continually capturing acoustic sample data that is displayed in real time to the user. When the user freezes the system, the user has the capability to view acoustic sample data previously captured in cine memory.

The CPU 30 controls the XY memory 24 and the cine memory 28 via the system control bus 34. In particular, the CPU 30 controls the flow of raw data from the XY memory 24 to the video processor 16 and to the cine memory 28 and from the cine memory to the video processor 16 and to the CPU 26 itself. The CPU also loads the gray maps and color maps into the video processor.

Image frames are collected in cine memory 28 on a continuous basis. The cine memory 28 provides resident digital image storage for single image review and multiple image loop review and various control functions. The region of interest displayed during single-image cine replay is that used during the image's acquisition. The cine memory also acts as a buffer for transfer of images to digital archival devices (not shown) via the master controller 26.

The preferred embodiment uses a system of the type described in FIGS. 1–4 to implement a technique for volumetric blood flow measurement combining standard Doppler measurements with echo amplitude decorrelation. Using single clinical transducer 2, and without knowledge of the orientation of a vessel in which fluid volume flow is to be measure, a 3-D vector flow field is computed over an ultrasound imaging plane. In general, volume flow is computed by integrating the out-of-plane flow (e.g., flow intersecting the imaging plane) over the vessel cross-section (i.e., the intersection of the imaging plane with the vessel).

In-plane Velocity

Figure 5:
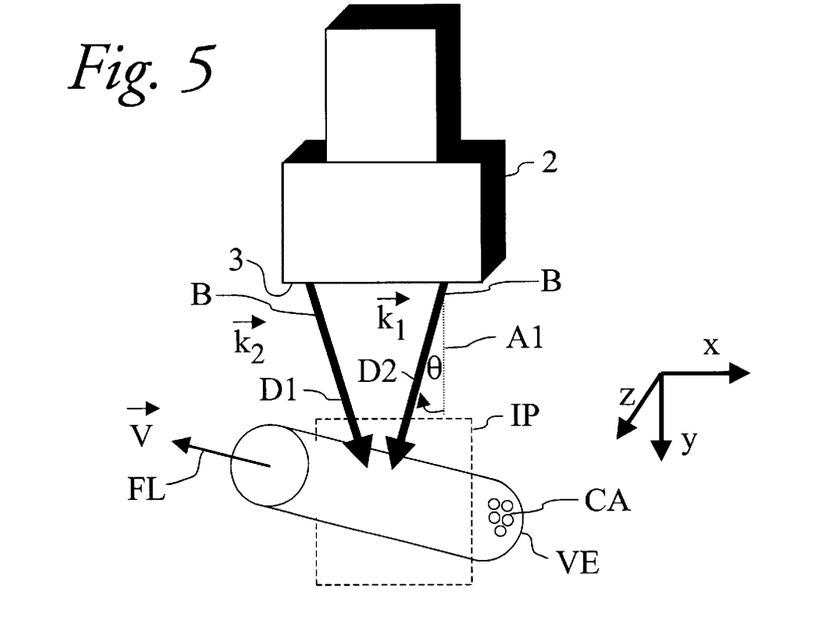
FIG. 5 is a schematic block diagram showing an exemplary orientation of the ultrasound transducer shown in FIG. 1 with respect to a vessel in which fluid is flowing.

FIG. 5 displays flow direction FL of fluid (e.g., blood) in a region of interest (which may be a vessel VE, e.g., a blood vessel) and orientation of transducer 2. The fluid preferably contains a contrast agent CA. Doppler ultrasound waves in a beam B are steered in directions D1 and D2 (e.g., θ=+20 degrees and −20 degrees from an axis A1 perpendicular to the face 3 of the transducer). The steering is accomplished using separate B-mode beam pulse firings. Directions D1 and D2 define an imaging and scan plane IP which intersects vessel VE at some undetermined angle, which may be, for example, 60 degrees, although the user does not know the angle. Any two dimensional method of directing beam B in plane IP may be used, such as triangulation, cross correlation, etc.). Alternatively, the scanning of beam B may be performed using the split aperture technique described in U.S. Pat. No. 5,398,216 (Hall et al., issued Mar. 14, 1995) which is incorporated by reference. Using the split aperture approach, beam B would be directed to a common point within vessel VE from different angles.

The x and y axes in FIG. 5 both lie in plane IP. The z axis extends in the elevational direction; the y axis extends in the axial direction and the x axis extends in the lateral direction. Axes x, y and z are orthogonal.

The ultrasound waves backscattered from vessel VE in response to the beam steered in directions D1 and D2 are received by transducer 2 and are used to generate data from which the two corresponding "axial" fluid velocities, $V_1$ and $V_2$ are measured. The in-plane (i.e., plane IP) fluid velocity components $V_x$ and $V_y$ can then be computed as follows:

$$V_1 = \vec{k}_1 \cdot \vec{V} = -V_x \sin\theta + V_y \cos\theta \quad (1)$$

$$V_2 = \vec{k}_2 \cdot \vec{V} = V_x \sin\theta + V_y \cos\theta \quad (2)$$

$$V_x = \frac{V_2 - V_1}{2\sin\theta} \text{ and } V_y = \frac{V_1 + V_2}{2\cos\theta} \quad (3)$$

Note that the measurement error for $V_y$ has an inverse cos (θ) dependency, so larger angles will provide more accurate results.

Decorrelation

The rate of speckle decorrelation in a fluid is a function of flow velocity or beam pulse repetition frequency (PRF) (depending on the processing method) and the beam characteristics of transducer 2. The rate of decorrelation can be calculated from color flow transmit firings of the type previously described. More specifically, the rate of decorrelation can be based on color flow power as expressed by the zero lag autocorrelation equation (C). The rate of decorrelation is determined by the change in value of R(0) over time from one pocket of firings to another.

The rate of decorrelation also can be calculated from gray scale data which represents ultrasound RF data backscattered from vessel VE. The rate of decorrelation based on gray scale data will be described in detail, but the principles can be applied to calculating the rate of decorrelation from color flow transmit firings by those skilled in the art. While a more detailed statistical analysis of speckle formation is given in a previous paper (Tuthill et al, 1998) [10], the essential points and assumptions are presented here.

For fully developed speckle, at least 10 scatterers must be present in the sample volume defined by the 3-D point spread function. The spatial distribution of ultrasonic intensity should be an exponential distribution with a constant mean to standard deviation (MSD) ratio of 1.0. The amount of speckle change from pulse to pulse (or frame to frame) is directly related to the second order statistics of the speckle pattern.

The derivation for the speckle correlation function in the elevational dimension (i.e., perpendicular to plane IP) is described here, and can easily be extended to the lateral and axial dimensions which are in plane IP. For coherently formed speckle, the intensity correlation function is directly related to the amplitude correlation function which in turn is proportional to the point spread function (PSF) autocorrelation. Assuming a focused transducer 2, the beam pattern can then be approximated by a Gaussian which has a depth-dependent width as the beam goes in and out of the focal region. Consequently, the intensity autocorrelation in the lateral direction can also be written as a Gaussian function with respect to the fluid translation between acquired frames and will have a standard deviation of $\sigma_x(z)$, the depth-dependent beam correlation width (BCW). The correlation width in the focus can be calculated by the transducer's physical properties, or the correlation width for a longer range can be calibrated using a phantom containing scatterers producing fully developed speckle.

The temporal normalized intensity covariance, C, for a single pixel location then has a Gaussian shape (Wear 1987) [11].

$$C(\Delta t, z) \propto \exp\left(\frac{-(V_x \Delta t)^2}{2\sigma_x^2(z)}\right) \quad (4)$$

where $V_x$ is the lateral velocity and $\sigma_x(z)$ is the depth-dependent beam correlation width as determined by the transducer properties. For a beam B pulse firing rate of $R_f$, the normalized covariance from a set of pixels at a specific depth acquired from consecutive A-lines can then be curve fit to a Gaussian as a function of the firing number, n, $$C(n) \propto \exp\left(\frac{-(D n / R_f)^2}{2}\right) \quad (5)$$

where D, the rate of decorrelation value in units of inverse seconds, is equivalent to the velocity divided by the beam correlation width for that depth. The final result is that by Gaussian curve-fitting the correlation function for speckle regions from a set of gray scale A-lines or from a set of gray scale B-scan frames, the average velocity for that set can be calculated. The rate of decorrelation can be calculated by the methods described in Tuthill (1998) [10] and Rubin (1999) [9], among others. Decorrelation may also be calculated from Doppler information (Adler 1995) [12] and (Chen 1996) [15], but may not be the preferred method for some applications.

For volume flow, the decorrelation can now be extended to include all 3 dimensions. Assuming an ellipsoidal sample volume, the curve-fitted decorrelation value, D, is directly related to the velocity components, $$D^2 = \frac{V_x^2}{B_x^2} + \frac{V_y^2}{B_y^2} + \frac{V_z^2}{B_z^2} \quad (6)$$

where $B_i$ is the beam correlation width (BCW) in the $i^{th}$ direction. The BCWs are calibrated using a speckle phantom and are dependent on depth and the transducer's focusing parameters, but are measurable throughout the imaging plane.

3-D Flow Vector and Volume Flow

Having determined the in-plane velocities, $V_x$ and $V_y$ (i.e., the velocities in plane IP), from the Doppler measurements (or from speckle tracking), the magnitude of the velocity component normal to the scan plane IP, Vz, can be computed from Equation (6). Thus the 3-D flow vector can be determined from a single transducer 2 operating in two different modes for three measurements (for example two Doppler and one grayscale decorrelation). It should be understood that the method of data collection and its processing to obtain each of the values $V_x$, $V_y$, and D can have many forms.

The total volume flow through vessel VE can also be computed. Gauss' theorem states that the flux or volume flow out of a closed surface equals the integral of the divergence of the vector field over the enclosed volume. Thus, the total volume flow, F, is the normal velocity component integrated over the cross-sectional area, $$F = \int (\vec{V} \cdot \vec{n}) ds \qquad (7)$$

By summing up Vz, the velocity components normal to the imaging and scan plane IP, over the vessel area intersected by plane IP, the total volume flow can be calculated. The calculations of equations (A)–(H) and (1)–(7) may be performed by CPU 30 (FIG. 4). CPU 30 generates signals corresponding to the various parameters of equations (A)–(H) and (1)–(7).

A variety of digital processors may be used to perform the calculations described in this specification. For example, microprocessors or digital signal processors, as well as application specific integrated circuits capable of performing logic and arithmetic operations, may be used. Such processors may be located anywhere in the system described in FIGS. 1–4, or may be located outside the system.

EXAMPLES

The following represents a best mode of the invention in the sense that it has been confirmed by experiment. However, it is believed that other forms of the invention, such as measuring decorrelation by color flow transmit firing, may be easier to implement for some applications.

A GE Logiq 700 clinical scanner (GE Medical Systems, Milwaukee, Wis.) with a 7.5 MHz linear array transducer was used with a single focus. The GE Logic 700 scanner can be generally represented by FIGS. 1–4 and the 7.5 MHz linear array transducer can be represented by transducer 2. All internal post-processing settings such as edge enhancement and averaging were turned off, and the depth was set to the minimum value of 3 cm to obtain the highest allowable frame rate of 30 Hz. The output power was set at the lowest level to reduce effects from additional decorrelation due to acoustic radiation force. For B-mode, a linear grayscale mapping was applied and the scans were decompressed to obtain images with pixel values proportional to amplitude. For the Doppler acquisition, the lowest velocity and lowest settings of wall filter 9 were applied. All images were digitally stored on the scanner at 8 bits and transferred to a UNIX computer which can be represented by CPU 30 (FIG. 4). The 3 cm by 4 cm digitized images were stored as 355 by 478 pixels for a square pixel size of length 84.5 $\mu$m in memory 32 (FIG. 4).

The transducer sample volume was calibrated by collecting a series of B-mode scans with incremental spacing in each direction (lateral, elevational, and axial) over a tissue-mimicking phantom (CIRS; Computerized Imaging Reference Systems, Norfolk, Va.). The phantom is comprised of densely packed, randomly distributed scatterers to create fully developed speckle. A linear micropositioner allowed for spacings of 50 $\mu$m for lateral and elevation directions, and 25 $\mu$m for axial. For each transducer orientation, a set of 60 images was acquired, and the corresponding beam correlation width was then computed as a function of depth.

For the flow tube experiments, a 6.4 mm diameter molecularporous membrane tube (Spectrum Laboratories, Laguna Hill, Calif.) was placed in a water bath filled with degassed water. A syringe pump (Harvard Apparatus, Holliston, Mass.) was used to generate flows from 12 to 20 ml/min. Care was taken not to introduce air bubbles into the tube system. The outlet of the system was kept 10 cm above the tank to maintain pressure and ensure full expansion of the membrane tubing.

The blood mimicking fluid was comprised of 1–35 $\mu$m diameter polystyrene spheres in a 5:1 water/glycerol mixture. A high concentration was used to increase the backscatter for more uniform speckle.

Transducer 2 was fixed to allow both rotation about the y-axis and x-axis independently as shown in FIG. 5. The transducer was rotated about the y-axis in 30° increments for each of three different volume flows.

For each volume flow setting, a cine loop of 60 grayscale images was collected first and stored in memory 28G (FIG. 4), followed by a set of Doppler images. Ten uncorrelated images were collected for each of the two Doppler angles (+/−20°) and then averaged.

The stored images were post-processed using programs written in MATLAB (Mathworks, Natwick, Mass.). For the speckle decorrelation, the covariance function was computed for each pixel and averaged over a 5 by 5 pixel window. The covariance function was then normalized, and only the first two lags were used for the Gaussian fit to determine the decorrelation value.

The resulting decorrelation image was thresholded to determine the outline of the vessel. Using Eq. 6, the out-of-plane velocity (i.e., velocity along the z axis as shown in FIG. 5) was computed and summed up in the enclosed vessel VE to determine the total volume flow.

To demonstrate the efficacy of the technique with ultrasound RF signals, the flow tube was used in a second setup using a Diasonics scanner (Diasonics Ultrasound, Milpitas, Calif.) with a 5.0 MHz linear array used as transducer 2. Since the RF acquisition of a cine loop had an extremely low frame rate, only M-mode data was collected for the decorrelation processing. This provided a firing rate of 786 Hz for acquired A-lines.

Results

Figure 6:
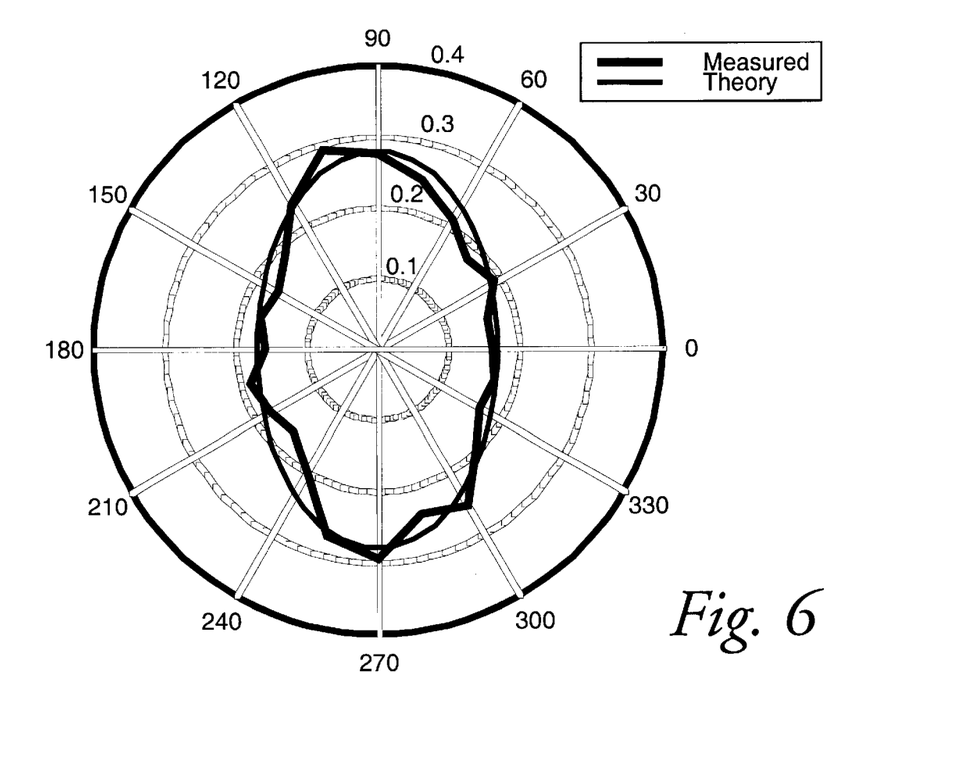
FIG. 6 is a graph illustrating calculated beam correlation widths of the ultrasound beam generated by the transducer shown in FIG. 5 for 15° increments about an elevational/lateral plane and a theoretical elliptical fit from $B_x$ (lateral) and $B_y$ (axial).

For the given scanner settings with a single focus, the GE 7.5 MHz transducer had BCWs of 170 $\mu$m, 280 $\mu$m, and 150 $\mu$m for the lateral, elevational, and axial directions, respectively, near the focus. FIG. 6 shows the calculated BCWs for 15° increments about the elevational/lateral plane and the theoretical elliptical fit from $B_x$ (lateral) and $B_y$ (elevational).

The calibration of the Diasonics transducer 2 using RF data showed that for both elevational and lateral directions, the depth dependent BCWs do not differ significantly from the envelope detected BCW curves. As expected, the axial RF signals decorrelate significantly faster than the envelope detected scan lines. Near the focus, the RF BCW is approximately 25 $\mu$m which is ⅙ of the total wavelength. The corresponding BCW for the envelope signal is 135 um which is consistent with a multiple wavelength pulse.

Both the −20° steering and the +20° steering (FIG. 5) Doppler images are used to form the combined total in-plane velocity magnitude image which may be displayed.

The thresholded decorrelation image was applied as a mask, and the normal velocities summed up in the enclosed region to compute the total volume flow. The decorrelation mask was chosen because it provides a detectable image of the vessel VE lumen regardless of flow angle, unlike the Doppler. The summed volume flow in the masked cross-sectional area is 0.25 ml/s.

For the algorithm described in this specification, the user needs only point at an area within vessel VE for the total cross-sectional area for that vessel to be determined from the thresholded decorrelation image. Using decorrelation thresholding with its reduced angle dependence (Rubin 1999) [9] should provide a more reliable delineation of the flow boundaries than would Doppler.

The spatial resolution for the velocity estimates computed with our technique is primarily limited by the Doppler signal which has a lower resolution than the B-mode images. The decorrelation technique is computed on each pixel in the B-scan or on each point of the A-line, and so the spatial resolution is determined by the digitizing sampling rate. Some spatial averaging is needed, however, to compute accurate correlation curves.

The temporal resolution is determined by the number of sequential A lines needed for an accurate estimate of the decorrelation and Doppler frequency shift. In most clinical scanners, approximately 10–15 firing lines are used to compute the Doppler output. Note that the inplane velocity could also be determined using 2 time correlation or speckle tracking.

Blood flow in humans range from 30 l/min in the aorta during strenuous exercise to 10 nl/min in a single capillary (velocity on the order of mm/s). Our technique does have both upper and lower limits on the range of velocities that can be measured. Low flows are difficult to detect using Doppler since a "wall-thump" filter is applied to eliminate signals from the relatively slow tissue motion. Similarly, decorrelation in soft tissue due to motion defines a lower bound.

At high velocities, the decorrelation component of the analysis breaks down. If the flow movement is more than two BCWs between firings, the signals are completely decorrelated and no velocity estimate can be made. Thus the PRF and the BCW of the sample volume determine the upper velocity limit: maximum velocity <PRF*(2 BCW). For example, with a 10 kHz firing rate and a correlation width of 400 $\mu$m, the maximum measurable velocity would be 80 cm/s. In the RF analysis, the axial BCW is an order of magnitude smaller than either the elevational or lateral component. Contrary to Doppler measurements, flow perpendicular to the beam is in the preferred direction to detect higher velocities.

The preferred technique also assumes flow all in one direction. Shear motion or turbulent flow may cause additional decorrelation which would upwardly bias the volume flow measurement. As previously described, examination of $\sigma^2$ can indicate this condition to avoid inappropriate use of the method.

The sign of flow cannot be determined in the decorrelation measurement. Thus the direction of out-of-plane flow remains unknown. This could be a problem with arterial flow where there may be reversal of flow during a heart cycle. One possibility to determine the flow directions would be phase quadrature analysis in the elevational direction with a 1.75 D array.

Those skilled in the art will recognize that the preferred embodiments may be altered and modified without departing from the true spirit and scope of the invention as defined in the accompanying claims.

What is claimed is:

1. An ultrasound system for measuring the volume of flow of a fluid within a region of interest, said system comprising in combination:
    a transducer arranged to generate and to transmit ultrasound waves to said region in transmit directions defining a scan plane, said transducer being arranged to generate transducer signals defining data in response to ultrasound waves backscattered from said fluid within said region; and
    a processor responsive to said data and arranged to calculate a first velocity signal having a first value representing a first component of velocity of said fluid flow in a first direction in said scan plane and a second velocity signal having a second value representing a second component of velocity of said fluid flow in a second direction in said scan plane, to correlate portions of said data, to calculate the rate of decorrelation of said portions, to calculate third velocity signals having third values representing third components of velocity of said fluid flow perpendicular to said scan plane in response to said first value, said second value and said rate of decorrelation, and to estimate said volume of fluid flow in response to said third velocity signals.

2. A system, as claimed in claim 1, wherein said transmit directions are defined by at least two different angles in said scan plane.

3. A system, as claimed in claim 2, wherein said transducer transmits said ultrasound waves by split aperture scanning.

4. A system, as claimed in claim 1, wherein said data defines gray scale data and wherein said processor correlates said portions of said gray scale data and calculates the rate of decorrelation of said portions of said gray scale data.

5. A system, as claimed in claim 4, where said gray scale data represents ultrasound RF data.

6. A system, as claimed in claim 4, wherein said gray scale data represents ultrasound A-line data.

7. A system, as claimed in claim 4, wherein said gray scale data represents ultrasound B-scan frames.

8. A system, as claimed in claim 1, wherein said data defines color flow power.

9. A system, as claimed in claim 1, wherein said portions of said correlated data represent speckle.

10. A system, as claimed in claim 9, wherein said speckle comprises fully developed speckle.

11. A system, as claimed in claim 1, wherein said processor calculates said velocity signals by Doppler calculations.

12. A system, as claimed in claim 1, wherein said second direction is perpendicular to said first direction.

13. A system, as claimed in claim 12, wherein said transducer signals define a beam which defines a first beam correlation width in said first direction, a second beam correlation width in said second direction, and a third beam correlation width in said third direction and wherein said processor generates said third velocity signals at least partially in response to said first, second and third beam correlation widths.

14. A system, as claimed in claim 1, wherein said processor estimates said volume of fluid flow by summing said third values over the cross sectional area of said region intersected by said scan plane.

15. A system, as claimed in claim 13, wherein said processor estimates said volume of fluid flow by summing said third values over the cross sectional area of said region intersected by said scan plane.

16. A system, as claimed in claim 1, wherein said fluid comprises blood and wherein said region comprises a blood vessel.

17. A system, as claimed in claim 1, wherein said fluid comprises a contrast agent.

18. In an ultrasound system, a method for measuring the volume of flow of a fluid within a region of interest, said method comprising:

transmitting ultrasound waves to said region in transmit directions defining a scan plane;

generating data signals defining data in response to ultrasound waves backscattered from said fluid within said region;

generating in response to said data a first velocity signal having a first value representing a first component of velocity of said fluid flow in a first direction in said scan plane and a second velocity signal having a second value representing a second component of velocity of said fluid flow in a second direction in said scan plane;

correlating portions of said data;

calculating the rate of decorrelation of said portions;

generating third velocity signals having third values representing third components of velocity of said fluid flow perpendicular to said scan plane in response to said first value, said second value and said rate of decorrelation; and estimating said volume of flow of said fluid in response to said third velocity signals.

19. A method, as claimed in claim 18, wherein said transmit directions are defined by at least two different angles in said scan plane.

20. A method, as claimed in claim 19, wherein transmitting comprises split aperture scanning.

21. A method, as claimed in claim 18, wherein said data defines gray scale data; wherein said correlating comprises correlating portions of said gray scale data and wherein said calculating the rate of decorrelation comprises calculating the rate of decorrelation of said portions of said gray scale data.

22. A method, as claimed in claim 21, wherein said gray scale data represents ultrasound RF data.

23. A method, as claimed in claim 21, wherein said gray scale data represents ultrasound A-line data.

24. A method, as claimed in claim 21, wherein said gray scale data represents ultrasound B-scan frames.

25. A method, as claimed in claim 18, wherein said data defines color flow power.

26. A method, as claimed in claim 18, wherein said portions of said correlated data represent speckle.

27. A method, as claimed in claim 26, wherein said speckle comprises fully developed speckle.

28. A method, as claimed in claim 18, wherein said generating velocity signals comprises calculating said velocity signals by Doppler calculations.

29. A method, as claimed in claim 18, wherein said second direction is perpendicular to said first direction.

30. A method, as claimed in claim 29, wherein said ultrasound waves form a beam defining a first beam correlation width in said first direction, a second beam correlation width in said second direction, and a third beam correlation width in said third direction and wherein said third velocity signals are generated at least partially in response to said first, second and third beam correlation widths.

31. A method, as claimed in claim 18, wherein said estimating comprises summing said third values over the cross sectional area of said region intersected by said scan plane.

32. A method, as claimed in claim 30, wherein said estimating comprises summing said third values over the cross sectional area of said region intersected by said scan plane.

33. A method, as claimed in claim 18, wherein said fluid comprises blood and wherein said region comprises a blood vessel.

34. A method, as claimed in claim 18, wherein said fluid comprises a contrast agent.

* * * * *